United States Patent [19]

Cook et al.

[11] Patent Number: 5,205,946
[45] Date of Patent: Apr. 27, 1993

[54] PROCESS FOR THE PRODUCTION OF OVERBASED CALIXARATES

[75] Inventors: Stephen J. Cook, North Humberside; Sean P. O'Conner, Reigate; Andrew Pearce, North Humberside, all of Great Britain

[73] Assignee: BP Chemicals (Additives) Limited, London, England

[21] Appl. No.: 831,964

[22] Filed: Feb. 6, 1992

Related U.S. Application Data

[62] Division of Ser. No. 674,509, Mar. 22, 1991, Pat. No. 5,114,601.

[30] Foreign Application Priority Data

Mar. 31, 1990 [GB] United Kingdom ............ 90/07314.9

[51] Int. Cl.$^5$ .................... C10M 145/00; C07C 35/22
[52] U.S. Cl. ........................................ 252/25; 252/18; 252/39; 568/631; 568/632; 568/633; 549/348
[58] Field of Search ............................ 252/18, 25, 39; 568/631, 632, 633; 549/348

[56] References Cited

U.S. PATENT DOCUMENTS

| | | | |
|---|---|---|---|
| 3,312,618 | 4/1967 | Le Suer et al. | 252/25 |
| 3,372,118 | 3/1968 | Rense | 252/25 |
| 3,857,790 | 12/1974 | Saunders et al. | 252/22 |
| 3,928,216 | 12/1975 | Saunders et al. | 252/18 |
| 4,032,514 | 6/1977 | Buriks et al. | 252/331 |
| 4,057,504 | 11/1977 | Shiga et al. | 252/25 |
| 4,435,301 | 3/1984 | Brannen et al. | 252/18 |
| 4,474,917 | 10/1984 | Burton | 252/49.8 |
| 4,477,377 | 10/1984 | Izatt et al. | 252/631 |
| 4,550,197 | 10/1985 | Shippey | 252/39 |
| 4,718,966 | 1/1988 | Harris et al. | 568/631 |
| 4,758,360 | 7/1988 | Beenasconi et al. | 252/25 |
| 4,775,490 | 10/1988 | Nichols et al. | 252/25 |
| 4,882,449 | 11/1989 | Harris | 568/25 |
| 5,043,415 | 8/1991 | Harris et al. | 568/631 |

FOREIGN PATENT DOCUMENTS

195048 8/1987 Japan.
1139172 1/1969 United Kingdom.

OTHER PUBLICATIONS

Calixarenes. 4. The Synthesis, Characterization, and Properties of the Calixarene from p-tert-Butylphenol, Gutsche et al. J. Amer. Chem. Soc. 1981.

*Primary Examiner*—Prince Willis, Jr.
*Assistant Examiner*—J. Silbermann
*Attorney, Agent, or Firm*—Brooks Haidt Haffner & Delahunty

[57] ABSTRACT

Non-sulphurized overbased metal salts of sulphur-free calixarenes having a substituent hydroxyl group or groups available for reaction with metal base and their preparation are claimed. The salts are useful as additives to lubricating oils by reason of their acids neutralization capability, their detergent and their antioxidant properties.

14 Claims, No Drawings

PROCESS FOR THE PRODUCTION OF OVERBASED CALIXARATES

This application is a division of application Ser. No. 07/674,509 filed Mar. 22, 1991, now U.S. Pat. No. 5,114,601.

The present invention relates generally to overbased metal salts, their preparation and their use as detergent additives in lubricating oil compositions.

In the operation of the internal combustion engine by-products from the combustion chamber often blow by the piston and admix with the lubricating oil.

Compounds generally employed to neutralise the acidic materials and disperse sludge within the lubricating oil are the overbased alkaline earth metal sulphurised hydrocarbyl-substituted phenates, salicylates, napthenates and sulphonates. The term "overbased" is generally used to describe those alkaline earth metal hydrocarbyl-substituted salts in which the ratio of the number of equivalents of the alkaline earth metal moiety to the number of equivalents of the acid moiety is greater than one, and is usually greater than 1.2 and may be as high as 4.5 or greater. In contrast, the equivalent ratio of alkaline earth metal moiety to acid moiety in "normal" or "neutral" alkaline earth metal hydrocarbyl-substituted salts is one, and in "low based" salts is less than one. Thus, the overbased material usually contains greater than 20% in excess of the alkaline earth metal present in the corresponding neutral material. For this reason overbased alkaline earth metal hydrocarbyl-substituted salts have a greater capability for neutralising acidic matter than do the corresponding neutral alkaline earth metal hydrocarbyl-substituted salts, though not necessarily an increased detergency power.

In the manufacture of the aforesaid sulphurised hydrocarbyl phenates, hydrogen sulphide is generated, which hydrogen sulphide is generally disposed of by burning, thereby producing sulphur dioxide, which is released to the atmosphere. Environmental concerns are growing over the use of sulphur-containing lubricant additives, due to the resulting sulphur dioxide emissions associated with lubricant combustion in service, as well as in additive production. In consequence, a desirable objective would be to develop sulphur-free overbased alkaline earth metal salts suitable for use as detergent additives in lubricating oils.

In furtherance of this objective the present invention in one aspect provides a non-sulphurised overbased metal salt of a sulphur-free calixarene having a substituent hydroxyl group or groups available for reaction with metal base.

For a review of calixarenes the reader is referred to 'Monographs in Supramolecular Chemistry' by C David Gutsche, Series Editor-J Fraser Stoddart, published by the Royal Society of Chemistry, 1989. Calixarenes having a substituent hydroxyl group or groups include homocalixarenes, oxacalixarenes, homooxacalixarenes and heterocalixarenes.

Suitable calixarenes may be represented by the formula:

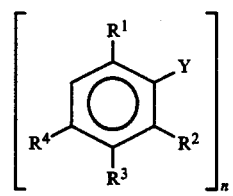

wherein
Y is a divalent bridging group;
$R^3$ is a hydrocarbyl or a hetero-substituted hydrocarbyl group;
either $R^1$ is hydroxyl and $R^2$ and $R^4$ are independently either hydrogen, hydrocarbyl or hetero-substituted hydrocarbyl, or
$R^2$ and $R^4$ are hydroxyl and $R^1$ is either hydrogen, hydrocarbyl or hetero-substituted hydrocarbyl; and
n is an integer in the range from 3 to 12.

In the formula (I), Y may suitably be $(CHR^6)_d$ in which $R^6$ is either hydrogen or hydrocarbyl e.g. of 1–6 carbons such as methyl and d is an integer which is at least one, n preferably is from 4 to 9. Any hetero substituted hydrocarbyl group has the heteroatom preferably O or NH interrupting a chain of carbon atoms, such as an alkoxy-alkyl group of 2–20 carbons.

A preferred calixarene has the formula:

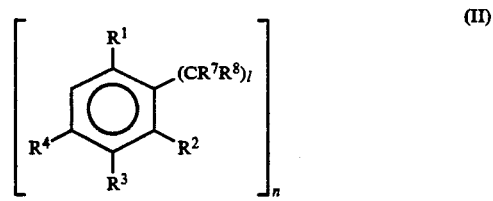

wherein $R^2$, $R^3$ and $R^4$ are independently either hydrogen, hydrocarbyl or hetero-substituted hydrocarbyl, either one of $R^7$ and $R^8$ is hydrogen and the other is either hydrogen or hydrocarbyl, n is an integer in the range 4 to 9, and e is one or greater e.g. 1–4.

Preferably in the formula (II), $R^2$ and $R^4$ are hydrogen, $R^3$ is hydrocarbyl e.g. of 1–20 such as 3–16 carbon atoms or hetero-substituted hydrocarbyl, more preferably alkyl, one of $R^7$ or $R^8$ is hydrogen and the other is either hydrogen or alkyl, n is either 4, 6 or 8 and e is one. In the case where one of $R^7$ or $R^8$ is alkyl, it is preferably $C_1$–$C_4$ alkyl, more preferably methyl. Preferably $R^3$ is alkyl, in particular nonyl (or a propylene trimer), t-butyl, dodecyl or tertiary-amyl. p-Alkylcalixarenes are also known as p-alkylphenol calixarenes and both terms will be used herein. An example of a suitable calixarene of the formula (II) is p-tert-butyl calix [6,8] arene. The [8] arene, for example, may be represented by the formula:

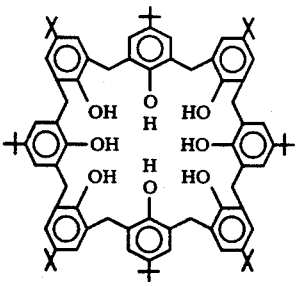

Other suitable calixarenes include p-dodecyl calix[6]arene, p-nonyl calix[8]arene and p-nonyl[6,7,8]arene.

Calixarenes may suitably be prepared by the method described in the aforesaid Monograph, Chapter 2. Typically, an alkyl phenol unsubstituted at the ortho-positions may be reacted in the presence of a base with an aldehyde, such as formaldehyde or acetaldehyde.

The metal moiety of the salts may suitably be either an alkali or an alkaline earth metal, or indeed any metal capable of forming salts with calixarenes. Preferred metals include calcium, magnesium or barium. A particularly preferred metal is calcium. The salts, will hereinafter be termed "calixarates". Overbased calixarates, the subject of the present invention, are calixarates in which the ratio of the number of equivalents of the metal moiety to the number of equivalents of the acid moiety is greater than one. In another aspect the present invention provides a process for the production of an overbased calixarate as hereinbefore described which process comprises reacting at elevated temperature:

(A) either (i) a sulphur-free calixarene having a substituent hydroxyl group or groups available for reaction with metal base, (ii) a low-based metal calixarate, (iii) a neutral metal calixarate or (iv) an overbased metal calixarate, (B) a metal base added either in a single addition or in a plurality of additions at intermediate points during the reaction, (C) A solvent comprising either:
  (C$_1$) either (i) a polyhydric alcohol having 2 to 4 carbon atoms, (ii) a di- (C$_3$ or C$_4$) glycol, (iii) a tri- (C$_2$–C$_4$) glycol or (iv) a mono- or poly-alkylene glycol alkyl ether of the formula:

wherein in the formula (III) R$^9$ is a C$_1$ to C$_6$ alkyl group, R$^{10}$ is an alkylene group e.g. 1–6 or 2–4 carbon atoms, R$^{11}$ is hydrogen or a C$_1$ to C$_6$ alkyl group and f is an integer from 1 to 6,
  either alone or in combination with either (C$_2$) a hydrocarbon solvent or C(3) either (i) water, (ii) a C$_1$ to C$_{20}$ monohydric alcohol, (iii) a C$_1$ to C$_{20}$ ketone, (iv) a C$_1$ to C$_{10}$ carboxylic acid ester or (v) an aliphatic, alicyclic or aromatic C$_1$ to C$_{20}$ ether, or,
  (C$_4$) a C$_1$ to C$_4$ monohydric alcohol, in combination with a hydrocarbon solvent (C$_2$), and (D) carbon dioxide added subsequent to each addition of component (B).

With regard to component (A) this may be either (i) a sulphur-free calixarene having a substituent hydroxyl group or groups available for reaction with metal base, (ii) a low-based calixarate, (iii) a neutral calixarate or (iv) an overbased calixarate. Suitable calixarenes (i) are those as hereinbefore described, particularly those alkyl calixarenes capable of conferring oil-solubility on the product. Preferred calixarenes include p-tert-butyl calix[6,8]arene, p-dodecyl calix[6]arene, p-nonyl calix[8]arene and p-nonyl calix[6,7,8]arene. Pre-formed calixarates wherein the equivalent ratio of metal base moiety to calixarene is either 1 (neutral calixarates) or less than 1 (low-based calixarates) may be employed to produce an overbased calixarate. Alternatively, an overbased calixarate according to the present invention may be employed, in which case the product is a calixarate having an increased degree of overbasing, i.e. a higher alkalinity value.

In addition to one of the alternatives (i) to (iv), component (A) may further include a compound of the general formula:

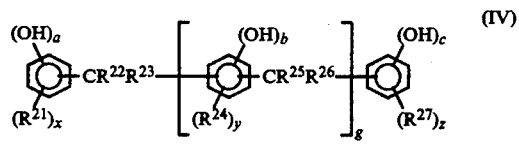

wherein a, b and c each independently represent 1 or 2; x, y and z each independently represent zero or an integer from 1 to 3;

R$^{21}$, R$^{24}$ and R$^{27}$ independently represent either hydrogen or a hydrocarbyl group, when x, y or z is greater than 1, each R$^{21}$, each R$^{24}$ or each R$^{27}$ respectively being the same or different;

R$^{22}$, R$^{23}$, R$^{25}$ and R$^{26}$ independently represent hydrogen or an alkyl group; and g is an integer from 1 to 20.

Preferred compounds of the formula (IV) are those in which a, b and C are 1; x, y and z are 1; R$^{21}$, R$^{24}$ and R$^{27}$ is preferably a C$_1$ to C$_{24}$ alkyl group, more preferably a C$_1$–C$_{12}$ alkyl group; either R$^{22}$=R$^{23}$=R$^{25}$=R$^{26}$= hydrogen or R$^{22}$=R$^{25}$= hydrogen and R$^{23}$=R$^{26}$= methyl; and g is preferably from 2 to 7, more preferably 3, Where R$^{22}$, R$^{23}$, R$^{25}$ and R$^{26}$ all represent hydrogen, the compound of general formula (IV) can be prepared by the condensation of the corresponding phenol with formaldehyde. Where one of R$^{22}$ and R$^{23}$ and one of R$^{25}$ and R$^{26}$ is hydrogen and the other is a hydrocarbyl group, for example a lower alkyl group, an aldehyde other than formaldehyde is used in the condensation with the phenol. Compounds of the formula (IV) are described in our copending UK application No. 9013317.4 (BP Case No. 7509) in relation to their alkali or alkali metal salts. The mixture of overbased salts and any low-based, neutral or unreacted compounds resulting from the use of the mixed feed is useful as a lubricating oil additive.

Component (B) is a metal base. The metal moiety may suitably be an alkali or alkaline earth metal, preferably an alkaline earth metal. The alkaline earth metal is preferably calcium, magnesium or barium, more preferably calcium. The base moiety may suitably be an oxide or a hydroxide, preferably the hydroxide. A calcium base may be added, for example, in the form of quick lime (CaO) or in the form of slaked lime (Ca(OH)$_2$) or mixtures of the two in any proportions. Component (B) may be added in whole to the initial reactants or in part to the initial reactants and the remainder in one or more further additions at intermediate points during the reaction.

Component (C) is a solvent for the reactants. The solvent (C) may be either (C₁) either alone or in combination with either (C₂) or (C₃), or the solvent (C) may be (C₄) in combination with (C₂) wherein:

(C₁) is either (i) a polyhydric alcohol having 2 to 4 carbon atoms, (ii) a di-(C₃ or C₄) glycol, (iii) a tri-(C₂ to C₄) glycol or (iv) a mono- or poly-alkylene glycol alkyl ether of the formula:

$$R^9(OR^{10})_f OR^{11} \qquad (III)$$

wherein in the formula (III) $R^9$ is a $C_1$ to $C_6$ alkyl group, $R^{10}$ is an alkylene group, $R^{11}$ is hydrogen or a $C_1$ to $C_6$ alkyl group and $f$ is an integer from 1 to 6. Suitable compounds having the formula (III) include the monomethyl or dimethyl ethers of (a) ethylene glycol, (b) diethylene glycol, (c) triethylene glycol or (d) tetraethylene glycol. A suitable compound is methyl diglycol ($CH_3OCH_2CH_2OCH_2CH_2OH$). Mixtures of glycol ethers of formula (V) and glycols may also be employed. The polyhydric alcohol may suitably be either a dihydric alcohol, for example ethylene glycol or propylene glycol, or a trihydric alcohol, for example glycerol. The di- ($C_3$ or $C_4$) glycol may suitably be dipropylene glycol, the tri- ($C_2$ to $C_4$) glycol may suitably be triethylene glycol. Preferably the component ($C_1$) is either ethylene glycol or methyl diglycol.

($C_2$) is a hydrocarbon solvent which may be aliphatic or aromatic. Examples of suitable hydrocarbons include toluene, xylene, naphtha and aliphatic paraffins, for example hexane, and cycloaliphatic paraffins.

($C_3$) may be either (i) water, (ii) a $C_1$ to $C_{20}$ monohydric alcohol, (iii) a $C_1$ to $C_{20}$ ketone, (iv) a $C_1$ to $C_{10}$ carboxylic acid ester or (v) an aliphatic, alicyclic or aromatic $C_1$ to $C_{20}$ ether. Examples are methanol, 2-ethyl hexanol, cyclohexanol, cyclohexanone, benzyl alcohol, ethyl acetate and acetophenone.

($C_4$) may be a $C_1$ to $C_4$ monohydric alcohol, preferably methanol.

Preferred solvents (C) comprise ethylene glycol, a mixture of ethylene glycol and 2-ethyl hexanol and a mixture of methanol and toluene.

Generally, in view of the intended use of the product, it is preferred to incorporate a lubricating oil as a solvent. The lubricating oil may suitably be an animal, a vegetable or a mineral oil. Suitably the lubricating oil is a petroleum-derived lubricating oil, such as a naphthenic base, paraffin i.e. base or mixed base oil. Solvent neutral oils are particularly suitable. Alternatively, the lubricating oil may be a synthetic lubricating oil. Suitable synthetic lubricating oils include synthetic ester lubricating oils, which oils include diesters such as di-octyl adipate, di-octyl sebacate and tri-decyladipate, or polymeric hydrocarbon lubricating oils, for example liquid polyisobutenes and poly-alpha olefins.

Component (D) is carbon dioxide, added subsequent to each addition of component (B). Carbon dioxide may be added in the form of a gas or a solid, preferably in the form of a gas. In gaseous form it may suitably be blown through the reaction mixture.

Preferably the reaction mixture may additionally incorporate as Component (E) either (i) a $C_6$ to $C_{100}$ carboxylic acid or an anhydride thereof, (ii) a di- or polycarboxylic acid containing from 36 to 100 carbon atoms or an anhydride thereof, (iii) a hydrocarbyl-substituted sulphonic acid or anhydride thereof, (iv) a hydrocarbyl-substituted salicylic acid or anhydride thereof, (v) a hydrocarbyl-substituted naphthenic acid or anhydride thereof, (vi) a hydrocarbyl-substituted phenol or (vii) a mixture of any two or more of (i) to (vi), of which (i) is preferred.

As regards (i), this is preferably an acid having the formula:

$$R^{12}-\underset{\underset{R^{13}}{|}}{CH}-COOH \qquad (V)$$

wherein $R^{12}$ is a $C_{10}$ to $C_{24}$ alkyl or alkenyl group and $R^{13}$ is either hydrogen, a $C_1$ to $C_4$ alkyl group or a $-CH_2COOH$ group. Preferably $R^{12}$ in the formula is an unbranched alkyl or alkenyl group. Preferred acids of formula (V) are those wherein $R^{13}$ is hydrogen and $R^{12}$ is a $C_{10}$ to $C_{24}$, more preferably $C_{18}$ to $C_{24}$ unbranched alkyl group. Examples of suitable saturated carboxylic acids of formula (V) include capric, lauric, myristic, palmitic, stearic, isostearic, arachidic, behenic and lignoceric acids. Examples of suitable unsaturated acids of formula (V) include lauroleic, myristoleic, palmitoleic, oleic, gadoleic, erucic, ricinoleic, linoleic and linolenic acids. Mixtures of acids may also be employed, for example rape top fatty acids. Particularly suitable mixtures of acids are those commercial grades containing a range of acids, including both saturated and unsaturated acids. Such mixtures may be obtained synthetically or may be derived from natural products, for example tall, cotton, ground nut, coconut, linseed, palm kernel, olive, palm, castor, soyabean, sunflower, herring and sardine oils and tallow.

Instead of, or in addition to, the carboxylic acid there may be used the acid anhydride, the acid chloride or the ester derivatives of the acid, preferably the acid anhydride. It is preferred however to use a carboxylic acid or a mixture of carboxylic acids. A preferred carboxylic acid of formula (V) is stearic acid. The acid may suitably be present in an amount up to 40% w/w, based on the total weight of the final product. It is believed that the acid, when present, chemically modifies the overbased calixarate product.

As regards (ii), this is preferably a polyisobutene succinic acid or a polyisobutene succinic anhydride.

As regards the hydrocarbyl substituent of (iii), (iv), (v) and (vi), this may suitably contain up to 125 aliphatic carbon atoms. Examples of suitable substituents include alkyl radicals, for example hexyl, cyclohexyl, octyl, isoctyl, decyl, tridecyl, hexadecyl, eicosyl and tricosyl, radicals derived from the polymerisation of both terminal and internal olefins, for example ethene, propene, 1-butene, isobutene, 1-hexene, 1-octene, 2-butene, 2-pentene, 3-pentene and 4-octene. Preferably the hydrocarbyl substituent is one derived from a polypropylene, poly-1-butene or polyisobutene.

The reaction mixture may also incorporate as component (F) a catalyst (or promoter) for the reaction. The catalyst may be an organic compound or an inorganic compound. Suitable organic compounds include (i) organic halides or (ii) organic alkanoates, which may suitably be represented by the formula:

$$R^{14}-X \qquad (VI)$$

wherein in the formula (VI) X is either halogen, suitably chlorine, bromine or iodine, preferably chlorine, or the group $OCOR^{15}$ wherein $R^{15}$ is suitably $C_1$ to $C_4$ alkyl and $R^{14}$ is either an alkyl, aryl or alkaryl group preferably having 3-20 or 6-20 or 7-20 carbons respectively, or halo-derivative thereof. Alternatively, the organic halide may be an HX salt of an organic base, for example guanidine hydrochloride. A suitable example of an organic halide of the formula (VI) is octyl chloride. Mixtures of (i) and (ii) may also be employed. Suitably the amount of organic compound (F) employed may be up to 2.0% by weight based on the weight of concentrate. Suitable inorganic compound catalysts include inorganic halides, particularly inorganic chlorides, and inorganic alkanoates. Examples of suitable inorganic compound catalysts include calcium acetate, calcium chloride, ammonium chloride, aluminium chloride and zinc chloride, of which calcium chloride and calcium acetate are preferred. Suitably the amounts of the inorganic compound catalyst employed may be up to 2.0% wt/wt based on the weight of the reaction mixture. Provided that the catalyst is present during the carbonation step, it may be added at any point in the process, though it will usually be found convenient to add the catalyst initially.

In order to produce an overbased calixarate from component (A)(i), (A)(ii) or (A)(iii) it is necessary only to react the (A) component with components (B), (C) and (D), using the appropriate proportions of components (A) and (B) to achieve overbasing. Suitably component (B) may be added in one or more additions, preferably in a single addition.

In order to produce a high TBN (Total Base Number) overbased calixarate, as an alternative to components (A)(i) to (iii) component (A)(iv) may be employed, and it is preferred to employ component (E), particularly either (E)(i) or (ii) and more particularly stearic acid, whilst at the same time adjusting the relative amounts of components (A) and (B) to a value sufficient to produce the high TBN desired. Again, component (B) may suitably be incorporated in one or more additions, preferably in a single addition.

Suitably the elevated temperature at which the process is operated may be a temperature in the range from 15° to 200° C., preferably from 50° to 175° C. The selection of the optimum temperature within the aforesaid range will depend to a large extent on the nature of the solvent employed.

Generally, the process will be operated in the presence of a lubricating oil. At the conclusion of the process it is preferred to recover the salt as a solution in lubricating oil by separating off volatile fractions, for example by distillation at subatmospheric pressure.

Finally, it is preferred to filter the solution. Alternatively, the solution may be centrifuged.

In another aspect the present invention also provides a composition suitable for use as an additive to lubricating oils which composition comprises as a first component an overbased calixarate as hereinbefore described and as a second component a neutral and/or an overbased metal salt of at least one of (i) a $C_6$ to $C_{100}$ carboxylic acid,
(ii) a di- or polycarboxylic acid containing from 36 to 100 carbon atoms,
(iii) a hydrocarbyl-substituted sulphonic acid,
(iv) a hydrocarbyl-substituted salicylic acid,
(v) a hydrocarbyl-substituted naphthenic acid or
(vi) a hydrocarbyl-substituted phenol.

Suitably the metal moiety of the salts in the composition may be either an alkali or an alkaline earth metal, preferably an alkaline earth metal, more preferably calcium, magnesium or barium.

The composition may be prepared simply by mixing the components. Preferably, however the composition is prepared by reacting components (A), (B), (C), (D) and (E), and optionally (F).

The overbased calixarates of the invention are useful in lubricating oil compositions both for their acids neutralisation capability and their detergent and antioxidant properties.

In a final aspect the present invention provides a finished lubricating oil composition which composition comprises a lubricating oil usually in a major proportion and an overbased alkaline earth metal salt of a calixarene as hereinbefore described, usually in a minor proportion; amounts of the calixarene salt may be 0.01-50% e.g. 0.1-35% by weight of the composition.

The finished lubricating oil composition may also contain effective amounts of one or more other types of conventional lubricating oil additives, for example viscosity index improvers, anti-wear agents, antioxidants, dispersants, rust inhibitors, pour-point depressants, or the like, which may be incorporated into the finished lubricating oil composition either directly or through the intermediacy of a concentrate composition.

The invention will now be further illustrated by reference to the following Examples. In all the Examples the term AV (Alkalinity Value) is used. AV is expressed in terms of mg KOH/g as measured by ASTM D2896. In the Examples where lime is used, it is in the form of slaked lime, $Ca(OH)_2$. Viscosities were measured by the method of ASTM D445.

EXAMPLE 1

| Initial charge | |
|---|---|
| p-t-Butyl Calix [6,8] arene | 75 g |
| Lubricating oil | 131 g |
| 2-Ethylhexanol | 224 g |
| Stearic acid | 70 g |
| Calcium chloride | 4 g |

Method (i) The initial charge was heated to 125° C. and lime (53 g) was charged,
(ii) the temperature was increased to 145° C. Ethylene glycol (36 g) was charged whilst ramping the temperature to 165° C.,
(iii) the mixture was held at 165° C. for 1 hour,
(iv) carbon dioxide (40 g) was added at 165° C./1 bar,
(v) the mixture was stripped at 200° C./10 mm Hg, and
(vi) the product was filtered through filteraid.

| RESULTS | |
|---|---|
| Product weight = | 340 g |
| Distillate weight = | 232 g |

| Product Composition After Filtration | |
|---|---|
| Ca = | 8.8% |
| Ca incorporation efficiency = | 99.5% |
| AV = | 233 mg KOH/g |
| $CO_2$ = | 7.6% |
| Viscosity at 100° C. = | 109 cSt |

EXAMPLES 2 TO 5

The procedure of Example 1 was repeated.

The reactants, their relative proportions and the results obtained for Examples 1 to 5 are given in the accompanying Table 1.

EXAMPLE 6

| Initial charge | |
|---|---|
| p-t-Butyl Calix [6,8] arene | 110 g |
| Lubricating oil | 131 g |
| 2-Ethylhexanol | 40 g |
| Stearic acid | 35 g |
| Calcium chloride | 4 g |
| Toluene | 200 g |
| Methanol | 20 g |

Method (i) The charge was heated to 60° C. and lime (76 g) was added,
(ii) the mixture was held at 60° C. for 1 hour,
(iii) carbon dioxide (57 g) was added at 60° C./1 bar,
(iv) methanol (10 g) and lime (35 g) were added at 60° C.,
(v) the mixture was held at 60° C. for 1 hour,
(vi) carbon dioxide (30 g) was added at 60° C./1 bar,
(vii) the mixture was stripped at 160° C./10 mm Hg, and
(viii) the product was filtered through filteraid.

| RESULTS | |
|---|---|
| Product weight = | 417 g |

| Product Composition After Filtration | |
|---|---|
| Ca = | 10.6% |
| Ca incorporation efficiency = | 71.9% |
| AV = | 290 mg KOH/g |
| $CO_2$ = | 6.8% |
| Viscosity at 100° C. = | 143 cSt |

EXAMPLE 7

The procedure of Example 6 was repeated.

The reactants, their relative proportions and the results obtained are given in the accompanying Table 1.

Comparison Test

The procedure of Example 6 was repeated except that the calixarene was omitted from the initial charge.

The reactants their relative proportions and the results obtained for Examples 6 and 7 are given in the accompanying Table 1.

EXAMPLE 8

| Initial charge | |
|---|---|
| p-t-Butyl Calix [6,8] arene | 75 g |
| Lubricating oil | 131 g |
| 2-Ethylhexanol | 224 g |

Method i) The initial charge was heated to 125° C. and lime (56 g) was charged,
ii) The temperature was increased to 145° C. Stearic acid (70 g) was charged,
iii) Ethylene glycol (36 g) was charged whilst ramping the temperature to 165° C.,
iv) The mixture was held at 165° C. for 1 hr.,
v) Carbon dioxide (55 g) was added at 165° C./1 bar,
vi) The mixture was stripped at 200° C./10 mm Hg, and
vii) The product was filtered through filteraid.

| RESULTS | |
|---|---|
| Product weight = | 338 g |

| Product Composition After Filtration | |
|---|---|
| Ca = | 8.6% |
| Ca incorporation efficiency = | 96% |
| AV = | 242 mg KOH/g |
| Viscosity at 100° C. = | 454 cSt |

EXAMPLE 9

The procedure of Example 8 was repeated. The reactants, their relative proportions and the results obtained are given in the accompanying Table 1.

EXAMPLES 10-11

The procedure of Example 8 was repeated except that p-Nonyl Calix [6,7,8] arene was used in place of p-t-butyl Calix [6,8] arene. The reactants, their relative proportions and the results obtained are given in the accompanying Table 1.

EXAMPLES 12-30

Nonylphenolcalix(6,8)arene in xylene solution (330 g of 13.64% solution, 0.03 moles) and SN150 diluent oil (90 g) were charged to a 1 liter, 5 necked, round bottomed, flange flask with take off condenser, thermopocket (with thermometer and thermocouple) and agitator (paddle type). The temperature of the mixture was raised to 110° C. and vacuum (29" Hg) applied to distil off the xylene. The vacuum was removed and while maintaining the temperature between 100° and 110° C., 2-ethylhexanol (222 g, 1.7 moles) was added, with stirring at approximately 500 rpm. The reaction mixture was raised to 130° C. and lime (58 g, 0.78 moles) was added over 5 minutes. Vacuum (10" Hg) was applied to the reactor and held for 15 minutes at 130° C. The vacuum was removed and stearic acid (100 g, 0.35 moles) was added over 10 minutes and vacuum (10" Hg) was reapplied to the reactor and held for 15 minutes at 130° C. The vacuum was removed and ethylene glycol (36 g, 0.58 moles) was added over 15 minutes and vacuum (10" Hg) was reapplied and the reaction held at 130° C. for 60 minutes. The vacuum was removed and CO2(58 g, 1.3 moles) was added over approximately 30–40 minutes. Vacuum (29" Hg) was applied and the temperature raised to 200° C. After 90 minutes, the vacuum was removed and the product cooled to 140° C. The product was filtered through a 15 mm deep pad of compressed clarcel DIC filter aid, supported on a no. 1 glass sinter funnel.

The batches of nonyl calixarate listed in Table 2 were manufactured in a similar manner as outlined above, however there are changes of conditions i.e. temperature, glycol and stearic acid. These are listed in Table 2.

EXAMPLES 31-37

Nonylphenolcalix(6,8)arene in xylene solution (330 g of 13.64% solution, 0.03 moles) and alkyl phenol with SN150 diluent oil (90 g) were charged to a 1 liter, 5 necked, round bottomed, flange flask with take off condenser, thermopocket (with thermometer and thermocouple) and agitator (paddle type). The temperature of the mixture was raised to 110° C. and vacuum (29" Hg) applied to distil off the xylene. The vacuum was removed and while maintaining the temperature between 100° and 110° C., 2-ethylhexanol (222 g, 1.7 moles) was added, with stirring at approximately 500 rpm. The reaction mixture was raised to 130° C. and lime (58 g, 0.78 moles) was added over 5 minutes. Vacuum (10" Hg) was applied to the reactor and held for 15 minutes at 130° C. The vacuum was removed and stearic acid (100 g 0.35 moles) was added over 10 minutes and vacuum (10" Hg) was reapplied to the reactor and held for 15 minutes at 130° C. The vacuum was removed and ethylene glycol (36 g, 0.58 moles) was added over 15 minutes and vacuum (10" Hg) was reapplied and the reaction held at 130° C. for 60 minutes. The vacuum was removed and $CO_2$ (58 g, 1.3 moles) was added over approximately 30-40 minutes. Vacuum (29" Hg) was applied and the temperature raised to 200° C. After 90 minutes, the vacuum was removed and the product cooled to 140° C. The product was filtered through a 15 mm deep pad of compressed Clarcel DIC filter aid, supported on a No 1 glass sinter funnel.

The batches of nonyl calixarate listed in Table 3 were manufactured in a similar manner as outlined above, however there are changes in the alkyl phenol used i.e. type or amount. These are listed in Table 3.

EXAMPLES 38-45

The alkyl calixarene in xylene solution (330 g of 13.64% solution, 0.03 moles) with SN150 diluent oil (90 g) were charged to a 1 liter, 5 necked, round bottomed, flange flask with take off condenser, thermopocket (with thermometer and thermocouple) and agitator (paddle type). The temperature of the mixture was raised to 110° C. and vacuum (29" Hg) applied to distil off the xylene. The vacuum was removed and while maintaining the temperature between 100° and 110° C., 2-ethylhexanol (222 g, 1.7 moles) was added, with stirring at approximately 500 rpm. The reaction mixture was raised to 130° C. and lime (58 g, 0.78 moles) was added over 5 minutes. Vacuum (10" Hg) was applied to the reactor and held for 15 minutes at 130° C. The vacuum was removed and stearic acid (100 g, 0.35 moles) was added over 10 minutes and vacuum (10" Hg) was reapplied to the reactor and held for 15 minutes at 130° C. The vacuum was removed and ethylene glycol (36 g 0.58 moles) was added over 15 minutes and vacuum (10" Hg) was reapplied and the reaction held at 130° C. for 60 minutes. The vacuum was removed and $CO_2$ (58 g, 1.3 moles) was added over approximately 30-40 minutes. Vacuum (29" Hg) was applied and the temperature raised to 200° C. After 90 minutes, the vacuum was removed and the product cooled to 140° C. The product was filtered through a 15 mm deep pad of compressed Clarcel DIC filter aid, supported on a No 1 glass sinter funnel.

The batches of alkyl calixarate listed in Tables 4 and 5 were manufactured in a similar manner as outlined above, however there are changes in the alkyl phenol and temperature of reaction used. These are listed in Tables 4 and 5.

TABLE 1

| Example | Carbonation Temp. (°C.) | REACTANTS Calix arene (g) | Stearic acid (g) | Catalyst | Lime (g) | $CO_2$ (g) | PRODUCT Filtration Rate | % Ca w/w | AV mg KOH/g | Viscosity at 100° C. (cSt) | % CIE |
|---|---|---|---|---|---|---|---|---|---|---|---|
| 1 | 165 | 75 | 70 | Solid $CaCl_2$ | 53 | 40 | A | 8.8 | 233 | 109 | 99.5 |
| 2 | 165 | 75 | 70 | Solid $CaCl_2$ | 53 | 26 | B | — | 240 | — | — |
| 3 | 165 | 110 | 35 | Solid $CaCl_2$ | 76 | 57 | C | 11.3 | 298 | — | 96.7 |
| 4 | 165 | 95 | 50 | Solid $CaCl_2$ | 76 | 61 | C | 11.8 | 320 | — | 95+ |
| 5 | 165 | 75 | 70 | Solid $CaCl_2$ | 56 | 63 | A | 9.1 | 251 | 140 | 97 |
| 6 | 60 | 110 | 35 | Solid $CaCl_2$ | 111 | 87 | B | 10.6 | 290 | 143 | 71.9 |
| 7 | 60 | 110 | 35 | Solid $CaCl_2$ | 76 | 57 | A | 7.0 | 189 | 195 | 59.4 |
| 8 | 165 | 75 | 70 | No Catalyst | 56 | 55 | A | 8.6 | 242 | 454 | 96 |
| 9 | 165 | 45 | 100 | No Catalyst | 56 | 55 | A | 9.0 | 258 | 278 | 94 |
| 10 | 165 | 45 | 100 | No Catalyst | 56 | 55 | A | 8.4 | 247 | 51 | 87 |
| 11 | 165 | 45 | 100 | No Catalyst | 85 | 85 | A | 11.5 | 363 | 171 | 72 |
| CT | 165 | 0 | 145 | No Catalyst | 56 | 55 | A | 9.2 | 248 | * | |

Abbreviations
CT = Comparison Test
Filtration Rate
A = Acceptable;
B = Difficult
C = Dilution with toluene prior to filtration necessary
CIE = Calcium incorporation efficiency
AV = Alkalinity Value
*Product solidified on standing

TABLE 2

| EXAMPLE | TEMP. (°C.) | GLYCOL (g) | STEARIC ACID (g) | CALIXARENE (g) | SN150 (g) | Ca (%) | V100 (Cst) |
|---|---|---|---|---|---|---|---|
| 12 | 130 | 36 | 100 | 330 | 90 | 9.86 | 173.4 |
| 13 | 130 | 36 | 80 | 330 | 90 | 10.47 | 153.6 |
| 14 | 110 | 36 | 100 | 330 | 90 | 10.04 | 182.2 |
| 15 | 110 | 36 | 80 | 330 | 90 | 10.48 | 90.3 |
| 16 | 130 | 30 | 100 | 330 | 90 | 8.56 | 139.2 |
| 17 | 130 | 30 | 80 | 330 | 90 | 8.68 | 94.1 |
| 18 | 110 | 30 | 100 | 330 | 90 | 11.13 | 268.6 |

TABLE 2-continued

| EXAMPLE | TEMP. (°C.) | GLYCOL (g) | STEARIC ACID (g) | CALIXARENE (g) | SN150 (g) | Ca (%) | V100 (Cst) |
| --- | --- | --- | --- | --- | --- | --- | --- |
| 19 | 110 | 30 | 80 | 330 | 90 | 10.86 | 130.9 |
| 20 | 130 | 36 | 100 | 264 | 90 | 10.49 | 138.8 |
| 21 | 130 | 36 | 80 | 264 | 90 | 10.47 | 145.8 |
| 22 | 110 | 36 | 100 | 264 | 90 | 11.34 | 104.7 |
| 23 | 110 | 36 | 80 | 264 | 90 | 11.27 | 126.7 |
| 24 | 130 | 30 | 100 | 264 | 90 | 10.56 | 163.1 |
| 25 | 130 | 30 | 80 | 264 | 90 | 10.92 | 151.7 |
| 26 | 110 | 30 | 100 | 264 | 90 | 11.26 | 155.0 |
| 27 | 110 | 30 | 80 | 264 | 90 | 11.95 | — |
| 28 | 130 | 36 | 80 | 330 | 90 | 10.84 | 162.3 |
| 29 | 130 | 36 | 80 | 363 | 90 | 11.19 | 130.2 |
| 30 | 130 | 36 | 60 | 363 | 130 | 8.86 | 63.6 |

NOTE
1) The change in temperature applies to every part of the reaction procedure from the addition of lime to the carbonation stage.
2) 36 g of glycol = 0.58 moles
   30 g of glycol = 0.48 moles
3) 100 g of stearic acid = 0.35 moles
   80 g of stearic acid = 0.28 moles
   60 g of stearic acid = 0.21 moles
4) 363 g of nonylphenol calix(6,8)arene = 0.033 moles
   264 g of nonylphenolcalix(6,8)arene = 0.024 moles

TABLE 3

| Ex | Alkyl DDP | Phenol NP (g) | Calixarene (g) | SN150 (g) | Ca (%) | V100 (Cst) |
| --- | --- | --- | --- | --- | --- | --- |
| 31 | 4.5 | — | 330 | 90 | 9.58 | 125.7 |
| 32 | 9.0 | — | 264 | 90 | 9.98 | 118.8 |
| 33 | — | 9.0 | 264 | 90 | 9.55 | 167.1 |
| 34 | — | 9.0 | 264 | 90 | 10.09 | 147.6 |
| 35 | 9.0 | — | 264 | 90 | 10.58 | 225.5 |
| 36 | 9.0 | — | 264 | 90 | 11.40 | 104.4 |
| 37 | 9.0 | — | 330 | 110 | 9.63 | 97.6 |

NOTE
1. DDP = Dodecylphenol
2. NP = Nonylphenol
3. 330 g of nonylphenolcalix (6,8)arene = 0.030 moles
4. 264 g of nonylphenolcalix(6,8)arene = 0.024 moles

TABLE 4

| Prep No | Alkyl Calixarene | (g) | Temperature (°C.) | SN150 (g) | Ca (%) | V100 (Cst) |
| --- | --- | --- | --- | --- | --- | --- |
| 38 | AMYL | 52.5 | 130 | 90 | 10.67 | 122.2 |
| 39 | p-DODECYL | 330 | 110 | 110 | 9.79 | 65.7 |
| 40 | p-DODECYL | 330 | 130 | 110 | 10.29 | 67.8 |

NOTE
1. 52.5 g of amyl phenolcalixarene (65% solution in petroleum distillate) = 0.03 moles
2. 330 g of p-dodecylphenolcalixarene = 0.03 moles

TABLE 5

| Prep No | Alkyl Calixarene | (g) | Temperature (°C.) | SN150 (g) | Ca (%) | V100 (Cst) |
| --- | --- | --- | --- | --- | --- | --- |
| 41 | A | 62.5 | 130 | 90 | 7.58 | 189.1 |
| 42 | B | 330 | 130 | 90 | 9.41 | 133.9 |
| 43 | B | 330 | 110 | 110 | 8.73 | 62.5 |
| 44 | B | 330 | 130 | 110 | 9.76 | 67.8 |
| 45 | C | 90 | 130 | 90 | 9.86 | 89.9 |

NOTE
1. 'A' is a mixture of t-butyl phenolcalixarene/t-butyl phenol formaldehyde resin/free t-butyl phenol (50% solution in xylene) = 0.03 moles.
2. 'B' is an alkyl phenolcalixarene made from alkyl phenol which contains about 65% of the para isomer and the alkyl group is dodecyl (13.64% solution in xylene) = 0.03 moles.
3. 'C' is a mixture of p-nonyl phenolcalixarene/p-nonyl phenol formaldehyde resin/free p-nonyl phenol (50% solution in xylene) = 0.03 moles.

We claim:

1. A process for the production of an overbased metal salt which comprises reacting at elevated temperature:
(A) either (i) available for reaction with metal base, (ii) a low based metal calixarate, (iii) a neutral metal calixarate or an non-sulphurized overbased metal salt of a sulphur-free calixarene having a substituent hydroxyl group or groups available for reaction with a metal base,
(B) a metal base added either in a single addition or in a plurality of additions at intermediate points during the reaction,
(C) a solvent comprising either: ($C_1$) either (i) a polyhydric alcohol having 2 to 4 carbon atoms, (ii) a di- ($C_3$ or $C_4$) glycol, (iii) a tri- ($C_2$-$C_4$) glycol or (iv) a mono- or poly-alkylene glycol alkyl ether of the formula:

$$R^9(OR^{10})_fOR^{11} \qquad (III)$$

wherein in the formula (III) $R^9$ is a $C_1$ to $C_6$ alkyl group, $R^{10}$ is an alkylene group, $R^{11}$ is hydrogen or a $C_1$ to $C_6$ alkyl group and f is an integer from 1 to 6, either alone or in combination with either ($C_2$) a hydrocarbon solvent or C(3) either (i) water, (ii) a $C_1$ to $C_{20}$ monohydric alcohol, (iii) a $C_1$ to $C_{20}$ ketone, (iv) a $C_1$ to $C_{10}$ carboxylic acid ester or (v) an aliphatic, alicyclic or aromatic $C_1$ to $C_{20}$ ether, or, ($C_4$) a $C_1$ to $C_4$ monohydric alcohol, in combination with a hydrocarbon solvent ($C_2$), and
(D) carbon dioxide added subsequent to each addition of component (B).

2. A process according to claim 1 wherein component (A) further includes a compound of the general formula:

$$(OH)_a\text{-Ar}(R^{21})_x\text{-}CR^{22}R^{23}\text{-}[(OH)_b\text{-Ar}(R^{24})_y\text{-}CR^{25}R^{26}]_g\text{-}(OH)_c\text{-Ar}(R^{27})_z \qquad (IV)$$

wherein in the formula (IV):
a, b and c each independently represent 1 or 2;
x, y and z each independently represent zero or an integer from 1 to 3;
$R^{21}$, $R^{24}$ and $R^{27}$ independently represent either hydrogen or a hydrocarbyl group when x, y or z is greater than 1, each $R^{21}$ each $R^{24}$ or each $R^{27}$ respectively being the same or different;
$R^{22}$, $R^{23}$, $R^{25}$ and $R^{26}$ independently represent hydrogen or an alkyl group; and g is an integer from 1 to 20.

3. A process according to claim 2 wherein the compound of the formula (IV) is one in which:
   a, b and c=1;
   x, y and z=1;
   $R^{21}$, $R^{24}$ and $R^{27}$ is a $C_1$-$C_{12}$ alkyl group;
   either $R^{22}=R^{23}=R^{25}=R^{26}=H$ or $R^{22}=R^{25}=H$ and $R^{23}=R^{26}=CH_3$, and
   g=2 to 7.

4. A process according to claim 1 wherein component (A) is a sulphur-free calixarene having a substituent hydroxyl group or groups available for reaction with metal base.

5. A process according to claim 1 wherein component (A) is an overbased metal salt of a sulphur-free calixarene having a substituent hydroxyl group or groups available for reaction with a metal base.

6. A process according to claim 1 wherein the metal base (B) is either quick lime (CaO) or slaked lime (Ca(OH)$_2$) or a mixture of the two in any proportions.

7. A process according to claim 1 wherein the solvent (C) comprises ethylene glycol.

8. A process according to claim 1 wherein the solvent (C) comprises a mixture of ethylene glycol and 2-ethyl hexanol.

9. A process according to claim 1 wherein the solvent (C) comprises a mixture of methanol and toluene.

10. A process according to claim 1 wherein the solvent (C) further incorporates a lubricating oil.

11. A process according to claim 1 wherein the reaction mixture further incorporates component (E) which is either (i) a $C_6$ to $C_{100}$ carboxylic acid or an anhydride thereof, (ii) a di- or polycarboxylic acid containing from 36 to 100 carbon atoms or an anhydride thereof, (iii) a hydrocarbyl-substituted sulphonic acid or anhydride thereof, (iv) a hydrocarbyl-substituted salicylic acid or anhydride thereof, (v) a hydrocarbyl-substituted naphthenic acid or anhydride thereof, (vi) a hydrocarbyl-substituted phenol or (vii) a mixture of any two or more of (i) to (vi).

12. A process according to claim 11 wherein component (E) is an acid having the formula:

(V)

wherein in the formula (V):
   $R^{12}$ is a $C_{10}$ to $C_{24}$ alkyl or alkenyl group; and $R^{13}$ is either hydrogen, a $C_1$ to $C_4$ alkyl group or a —CH$_2$COOH group.

13. A process according to claim 11 wherein component (E) is stearic acid.

14. A process according to claim 1 wherein the reaction mixture further incorporates component (F) which is a catalyst (or promoter) for the reaction, which catalyst or promoter is either calcium acetate or calcium chloride.

* * * * *

UNITED STATES PATENT AND TRADEMARK OFFICE
CERTIFICATE OF CORRECTION

PATENT NO. : 5,205,946
DATED : April 27, 1993
INVENTOR(S) : STEPHEN J. COOK, SEAN P. O'CONNOR and ANDREW PEARCE It is certified that error appears in the above-indentified patent and that said Letters Patent is hereby corrected as shown below:

Col. 2, lines 1-10, formula (I) should read:

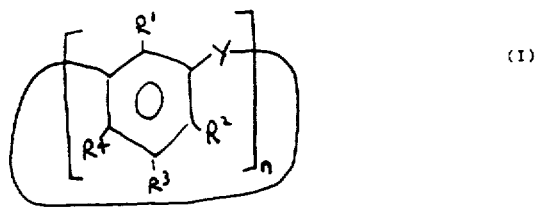

Col. 2, lines 35-45, formula (II) should read:

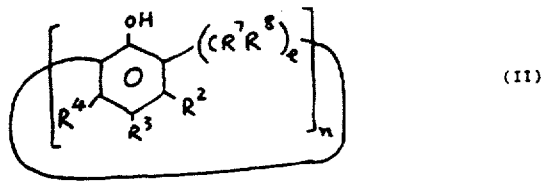

Signed and Sealed this

Fourth Day of October, 1994

Attest:

BRUCE LEHMAN

Attesting Officer  Commissioner of Patents and Trademarks